(12) United States Patent
Shelchuk

(10) Patent No.: US 8,233,979 B1
(45) Date of Patent: Jul. 31, 2012

(54) DISTRIBUTED ANODE CARDIAC PACING AND SENSING

(75) Inventor: Anne Shelchuk, Cupertino, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1037 days.

(21) Appl. No.: 11/688,941

(22) Filed: Mar. 21, 2007

(51) Int. Cl.
*A61N 1/00* (2006.01)
*A61B 5/00* (2006.01)

(52) U.S. Cl. ............. 607/9; 607/119; 600/374; 600/393

(58) Field of Classification Search .............. 607/9, 119; 600/374, 393
See application file for complete search history.

(56) References Cited

U.S. PATENT DOCUMENTS

| | | | |
|---|---|---|---|
| 4,922,607 A | 5/1990 | Doan et al. | |
| 4,995,389 A | 2/1991 | Harris | |
| 5,246,014 A | 9/1993 | Williams et al. | |
| 5,324,327 A * | 6/1994 | Cohen | 607/122 |
| 5,325,870 A * | 7/1994 | Kroll et al. | 607/122 |
| 5,350,410 A | 9/1994 | Kleks et al. | |
| 5,584,873 A | 12/1996 | Shoberg et al. | |
| 5,948,014 A | 9/1999 | Valikai | |
| 6,085,117 A * | 7/2000 | Griffin et al. | 607/5 |
| 6,466,810 B1 | 10/2002 | Ward et al. | |
| 6,546,288 B1 | 4/2003 | Levine | |
| 6,640,136 B1 | 10/2003 | Helland et al. | |
| 6,882,887 B1 | 4/2005 | Shelchuk et al. | |
| 6,978,178 B2 | 12/2005 | Sommer et al. | |
| 7,027,852 B2 | 4/2006 | Helland | |
| 7,123,969 B1 | 10/2006 | Chitre | |
| 2002/0103523 A1* | 8/2002 | Helland et al. | 607/122 |
| 2002/0123784 A1* | 9/2002 | Westendorp | 607/122 |
| 2005/0246003 A1* | 11/2005 | Black et al. | 607/116 |
| 2005/0288761 A1* | 12/2005 | Brabec et al. | 607/122 |
| 2006/0058588 A1 | 3/2006 | Zdeblick | |

* cited by examiner

*Primary Examiner* — Nicole F Lavert
(74) *Attorney, Agent, or Firm* — Steven M. Mitchell

(57) ABSTRACT

Embodiments of the present invention are directed to devices, systems and methods for pacing and sensing, in a chamber of a patient's heart, that provide for good sensed R wave amplitudes and capture thresholds, yet avoids extracardiac stimulation. Such benefits are achieved by using what is referred to herein as a "distributed" anode, where one portion of the anode is within 5 mm of the cathode, but another portion of the anode is at least 10 mm from the cathode. While especially useful for pacing and sensing in the left ventricle, embodiments of the present invention can be used to pace and sense in any chamber of the heart.

25 Claims, 8 Drawing Sheets

DISTRIBUTED ANODE CARDIAC PACING AND SENSING

FIELD OF THE INVENTION

The present invention generally relates to devices, systems and methods for providing cardiac pacing and sensing.

BACKGROUND

Pacing of the left side of the heart (i.e., left ventricle and/or left atrium) has been used, e.g., to improve cardiac function in heart failure patients. A challenge with such left side pacing is that undesirable extracardiac stimulation often occurs, especially of the diaphragm and/or the phrenic nerve.

The left phrenic nerve, which provides innervation for the diaphragm, arises from the cervical spine and descends to the diaphragm through the mediastinum where the heart is situated. As it passes the heart, the left phrenic nerve courses along the pericardium, superficial to the left atrium and left ventricle. Because of its proximity to electrodes used for left side pacing, the phrenic nerve can be inadvertently stimulated by a pacing pulse. Such phrenic nerve stimulation and/or more direct stimulation of the diaphragm can result in involuntary contraction of the patient's diaphragm, which can be similar to a hiccup, and annoying to the patient. Other types of inadvertent extracardiac stimulation that may occur include stimulation of the patient's pectoral muscles overlying implanted electrodes.

When implanting a left ventricular and/or atrial lead, physicians are faced with the limitations of the cardiac venous anatomy. Additionally, physicians are often faced with a potentially mottled ventricular myocardium for achieving adequate pacing and sensing thresholds. Further, physicians should also ensure that the implanted lead does not unacceptably stimulate extracardiac structures. If the lead does result in unacceptable extracardiac stimulation, then mechanical repositioning typically needs to be performed, which can be time consuming and costly. Accordingly, it would be advantageous to reduce the probability of undesirable extracardiac stimulation caused when attempting to pace the left side of the heart.

SUMMARY

Embodiments of the present invention are directed to devices, systems and methods for pacing and sensing, in a chamber of a patient's heart, that provide for good sensed R wave amplitudes and capture thresholds, yet avoid extracardiac stimulation. Such benefits are achieved by using what is referred to herein as a "distributed" anode, where one portion of the anode is within 5 mm of the cathode, but another portion of the anode is at least 10 mm from the cathode. While especially useful for pacing and sensing in the left ventricle, embodiments of the present invention can be used for pacing and sensing in any chamber of the heart.

Specific embodiments of the present invention related to methods for pacing and sensing in a chamber of a patient's heart using a lead that includes a first group of at least two electrically isolated electrodes within 5 mm of one another. As defined herein, electrodes within 5 mm of one another are considered to be electrodes within a same group, and electrodes within different groups are at least 10 mm from one another. In accordance with specific embodiments, when both pacing and sensing, at least one of the electrodes of a first group is used as the cathode, and at least one of the electrodes of the first group (that is not used as the cathode) together with a further electrode that is at least 10 mm from the first group are used as the "distributed" anode. This can be accomplished by appropriately configuring switches of an implantable cardiac device to enable pacing circuitry to pace in a chamber of the patient's heart, and sensing circuitry to sense in the chamber of the patient's heart, using as the cathode at least one of the electrodes of the first group, and using as the anode at least one of the electrodes of the first group (that is not used as the cathode) together with a further electrode that is at least 10 mm from the first group.

In certain embodiments, the same lead that includes the first group of electrodes can also include the further electrode, which can be, e.g., a ring or coil electrode, but is not limited thereto. In specific embodiments, the lead includes a first conductor and a second conductor, with one of the electrodes of first group hardwired to the first conductor, another one of the electrodes of first group hardwired to the second conductor, and the further electrode (which is at least 10 mm from the first group of electrodes) also hardwired to the second conductor. In other embodiments, the further electrode can be hardwired to a third conductor, and the second and third conductors can be connected by switches to thereby electrically connect the one of the electrodes of the first group with the further electrode as the distributed anode. In alternative embodiments, the further electrode (which is used as part of the distributed anode) can be an electrode of another lead.

In accordance with an embodiment, the conductive housing of the implantable cardiac stimulation device to which the lead is connected can be used as part of the "distributed" anode, together with the at least one of the electrodes of the first group that is not used as the cathode.

In certain embodiments, the same lead having the first group of electrodes also has a second group of at least two electrically isolated electrodes within 5 mm of one another, which are at least 10 mm from the first group. In such embodiments, at least one of the electrodes of the first group (that is not used as the cathode) can be used together with at least one of the electrodes of the second group as the "distributed" anode.

In specific embodiments, the lead includes a first conductor and a second conductor, and each group of electrodes of the lead includes switching circuitry to selectively connect each electrode of the group to either of the conductors. For use as the cathode, the switching circuitry of the first group can connect at least one of the electrodes of the first group to the first conductor. For use as the "distributed" anode, the switching circuitry of the first group can connect at least one of the electrodes of the first group (not connected as the cathode) to the second conductor and the switching circuitry of the second group can connect at least one of the electrodes of the second group also to the second conductor.

This summary is not intended to be a complete description of, or limit the scope of, the invention. Alternative and additional features, aspects, and objects of the invention can be obtained from a review of the specification, the figures, and the claims.

BRIEF DESCRIPTION OF THE DRAWINGS

The above, and further features, advantages and benefits of the present invention will be apparent upon consideration of the present description taken in conjunction with the accompanying drawings, briefly described below.

DETAILED DESCRIPTION

Figure 1:
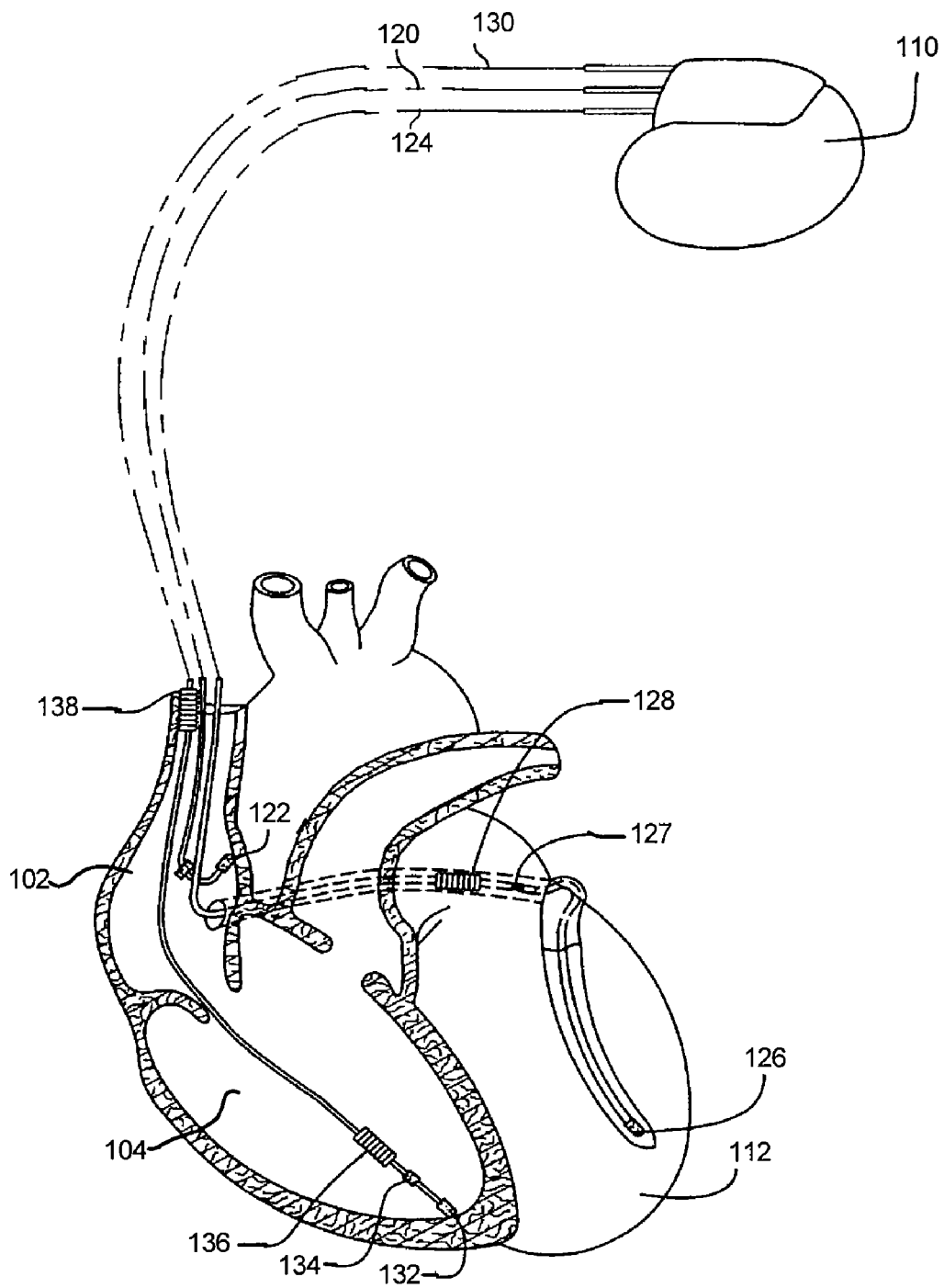
FIG. 1 is a simplified, partly cutaway view illustrating an exemplary implantable cardiac stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Exemplary Implantable Cardiac Stimulation Device

FIG. 1 illustrates an exemplary cardiac stimulation device 110 in electrical communication with a patient's heart 112 by way of three leads 120, 124 and 130 suitable for sensing cardiac electrogram signals and also delivering multi-chamber stimulation and shock therapy. To sense atrial cardiac signals and to provide right atrial chamber stimulation therapy, the cardiac stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the cardiac stimulation device 110 is coupled to a "coronary sinus" lead 124 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 124 is designed to receive atrial and ventricular cardiac signals and to deliver left ventricular pacing therapy using at least a left ventricular tip electrode 26, left atrial pacing therapy using at least a left atrial ring electrode 127, and shocking therapy using at least a left atrial coil electrode 128.

The cardiac stimulation device 110 is also shown in electrical communication with the patient's heart 12 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 32 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle.

Figure 2:
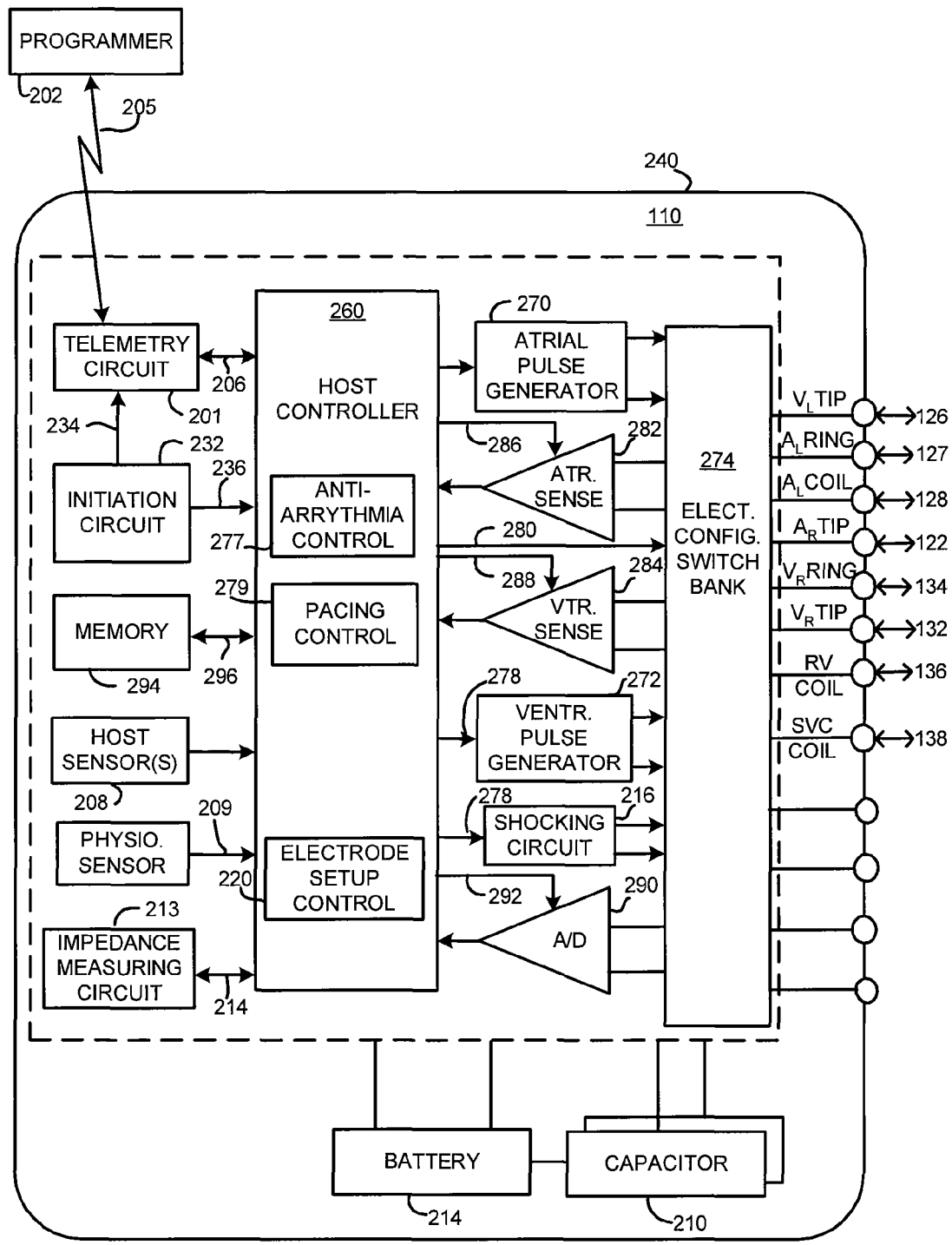
FIG. 2 is a functional block diagram of the exemplary multi-chamber implantable cardiac stimulation device of FIG. 1, illustrating the basic elements that provide cardioversion, defibrillation and/or pacing stimulation in four chambers of the heart.

FIG. 2 illustrates a simplified block diagram of the multi-chamber implantable cardiac stimulation device 110 which is capable of sensing cardiac electrogram signals, and also treating both fast and slow arrhythmias with stimulation therapy, including cardioversion, defibrillation, pacing stimulation. While a particular multi-chamber cardiac stimulation device is shown, this is for illustration purposes only and one of skill in the art could readily duplicate, eliminate or disable the appropriate circuitry in any desired combination to provide a device capable of sensing cardiac electrogram signals, treating the appropriate chamber(s) with cardioversion, defibrillation and/or pacing stimulation without departing from the scope of the invention.

Referring to FIG. 2, cardiac stimulation device 110 includes a housing 240 which is often referred to as a "can", "case" or "case electrode", and which may be programmably selected to act as the return electrode for all "unipolar" modes. Housing 240 may be used as a return electrode alone or in combination with one or more of the coil electrodes 128, 136, or 138, for shocking purposes. Housing 240 further includes a connector (not shown) having a plurality of terminals, 242, 244, 246, 248, 252, 254, 256, and 258 (shown schematically and, for convenience, the names of the exemplary electrodes to which they are connected are shown next to the terminals).

To achieve right atrial sensing and pacing, the connector includes at least a right atrial tip terminal 242 adapted for connection to the right atrial (AR) tip electrode 122. To achieve left chamber sensing, pacing and/or shocking, the connector includes at least a left ventricular (VL) tip terminal 244, a left atrial (AL) ring terminal 246, and a left atrial (AL) shocking terminal (coil) 248, which are adapted for connection to the left ventricular tip electrode 126, the left atrial ring electrode 127, and the left atrial coil electrode 128, respectively. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively.

At the core of cardiac stimulation device 110 is a programmable microcontroller, host controller 260, which controls the various modes of stimulation therapy. As is well known in the art, host controller 260 includes a microprocessor, or equivalent control circuitry or processor, designed for controlling the delivery of stimulation therapy, and may further include RAM or ROM memory, logic and timing circuitry, state machine circuitry, and I/O circuitry. Typically, host controller 260 includes the ability to process or monitor input signals (data) as controlled by program code stored in a designated block of memory. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2, an atrial pulse generator 270 and a ventricular pulse generator 272 generate pacing stimulation pulses for delivery by the right atrial lead 120, the right ventricular lead 130, and/or the coronary sinus lead 124 via a switch bank 274. It is understood that in order to provide stimulation therapy in each of the four chambers of the heart, the atrial pulse generator 270 and the ventricular pulse generator 272 may include dedicated, independent pulse generators, multiplexed pulse generators, or shared pulse generators. The atrial pulse generator 270 and the ventricular pulse generator 272 are controlled by host controller 260 via appropriate control signals 276 and 278, respectively, to trigger or inhibit the stimulation pulses.

Host controller 260 further includes pacing control unit 279 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

The switch bank 274 includes a plurality of electrically configurable switches for connecting the desired electrodes to the appropriate I/O circuits, thereby providing complete electrode programmability. Accordingly, the switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave. The switches of the switch bank 274 can be used to configure certain electrode(s) as the cathode, and certain electrodes as the anode, when pacing and sensing in accordance with embodiments of the present invention.

Atrial sensing circuits 282 and ventricular sensing circuits 284 may also be selectively coupled to the right atrial lead 120, coronary sinus lead 124, and the right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. The switch bank 274 determines the "sensing polarity" of the cardiac signal by selectively closing the appropriate switches. In this way, the clinician may program the sensing polarity independent of the stimulation polarity. Each of the sensing circuits, 282 and 284 preferably employ one or more low power, precision amplifiers with programmable gain and/or automatic gain control, bandpass filtering, and a threshold detection circuit, to selectively sense the cardiac signal of interest. The automatic gain control enables the cardiac stimulation device 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

Cardiac signals are also applied to the inputs of an analog-to-digital (A/D) data acquisition system 290. Data acquisition system 290 is configured to acquire intracardiac electrogram signals, convert the raw analog data into digital signals, and store the digital signals for later processing and/or telemetric transmission to an external device 202. Data acquisition system 290 is coupled to the right atrial lead 120, the coronary sinus lead 124, and the right ventricular lead 130 through switch bank 274 to sample cardiac signals across any pair of desired electrodes. Data acquired by data acquisition system 290 (and optionally stored) can be used for subsequent analysis to guide the programming of the device, appropriately adjust pacing interval parameters, select optimum pacing intervals, and/or select appropriate anti-arrhythmia therapy.

Advantageously, data acquisition system 290 may be coupled to host controller 260 or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition system 290 via control signal 292 to sample the cardiac signal that falls in the capture detection window and, based on the amplitude of the sampled cardiac signal, determines if capture has occurred. The capture threshold is defined as the lowest stimulation pulse energy at which capture occurs.

One function of the cardiac stimulation device 110 is to operate as an implantable cardioverter/defibrillator ("ICD") device. That is, cardiac stimulation device 110 detects the occurrence of an arrhythmia, and automatically applies an appropriate electrical shock therapy to the heart aimed at terminating the detected arrhythmia. To this end, anti-arrhythmia control unit 277 of control host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by host controller 260. Such shocking pulses are applied to the patient's heart through at least two shocking electrodes, as shown in this embodiment, selected from the left atrial coil electrode 128, the RV coil electrode 136, and/or the SVC coil electrode 138 (FIG. 1). As noted above, the housing 240 may act as an active electrode in combination with the RV electrode 136, or as part of a split electrical vector using the SVC coil electrode 138 or the left atrial coil electrode 128 (e.g., using the RV electrode as a common electrode). The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

For arrhythmia detection, the anti-arrhythmia control unit 277 of host controller 260 utilizes the atrial and ventricular sensing circuits 282 and 284 to sense cardiac signals, for determining whether a rhythm is physiologic or pathologic. The timing intervals between sensed events (e.g., P-waves, R-waves, and depolarization signals associated with fibrillation which are sometimes referred to as "F-waves" or "Fib-waves") are then classified by anti-arrhythmia control unit 277 of host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Host controller 260 is further coupled to a memory 294 by a suitable data/address bus 296, where the programmable operating parameters used by host controller 260 are stored and modified, as required, in order to customize the operation of the cardiac stimulation device 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 112 within each respective tier of therapy. A feature of the cardiac stimulation device 110 is the ability to sense and store a relatively large amount of data (e.g., from data acquisition system 290), which data may then be used for subsequent analysis and also guiding the programming of the cardiac stimulation device 110.

Advantageously, the operating parameters of the cardiac stimulation device 110 may be non-invasively programmed into the memory 294 through a telemetry circuit 201 in telemetric communication with an external programmer 202, such as a, transtelephonic transceiver, or a diagnostic system analyzer. Additionally, telemetry circuit 201 may be used to guide the device 110 through electrode setup algorithms of the present invention.

A handshake signal can be sent from the programmer 202 (or other external device) to the telemetry circuit 201 so that the external device can be identified to the telemetry circuit 201 thereby defining what operations may be performed by the device. The programmer 202 can program the cardiac stimulation device 110 under the control of a physician as described in more detail with respect to FIG. 3. For examples of such programmers, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (note: this relates to transfer of EGM data) (McClure et al.), which patents are hereby incorporated herein by reference.

Cardiac stimulation device 110 further includes initiation circuit 232. Initiation circuit 232 may comprise magnet detection circuitry. Initiation circuit 232 is coupled to host controller 260 by connection 236 and/or to telemetry circuit 201 by connection 234. The purpose of the initiation circuit is to detect an initiation signal from outside the patient. For example, a magnet placed over the cardiac stimulation device 110 may be used as the initiation signal, which signal may be used by a clinician to initiate various test functions of the cardiac stimulation device 110 and/or to signal host controller 260 that an external programmer 202 is in place to receive or transmit data to host controller 260 through the telemetry circuit 201.

An electrode setup control unit 220 of host controller 260 processes EGM signals to monitor for capture during pacing and to measure R-waves during sensing. The electrode setup control unit 220 can be used to configure switches of the switch bank 274 so that specific electrode(s) is/are connected as a cathode and specific electrodes are connected as an anode, in accordance with embodiments of the present invention.

Cardiac stimulation device 110 additionally includes a power source such as a battery 210 that provides operating power to all the circuits shown in FIG. 2. For a cardiac stimulation device 110, which employs shocking therapy, the battery 210 must be capable of operating at low current drains for long periods of time and also be capable of providing high-current pulses (for charging capacitor 210) when the patient requires a shock pulse. Battery 210 must preferably have a predictable discharge characteristic so that elective replacement time can be detected. Accordingly, cardiac stimulation device 110 can employ lithium/silver vanadium oxide batteries.

Exemplary Programmer

Figure 3:
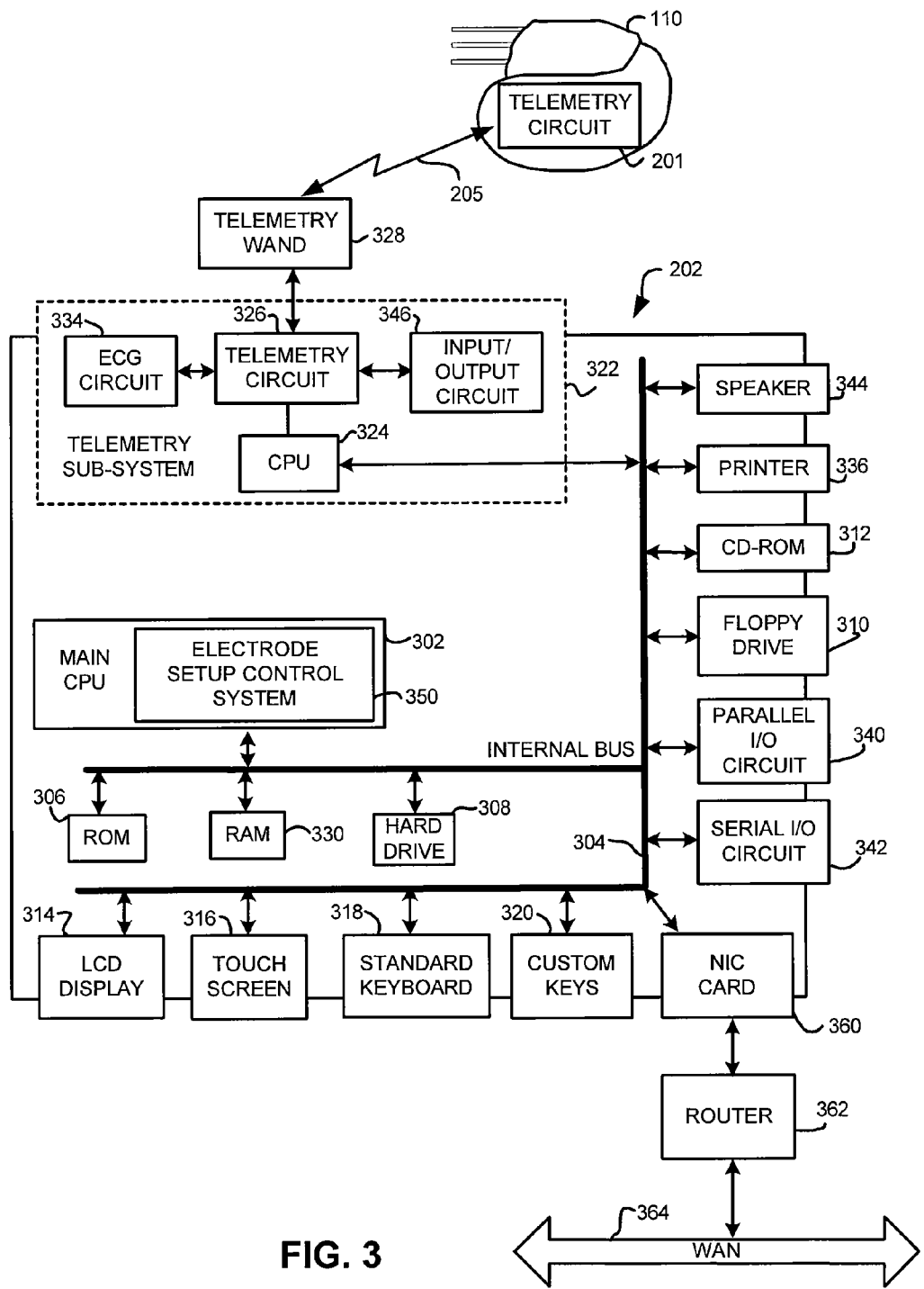
FIG. 3 is a functional block diagram illustrating components of an exemplary programmer for use in programming the implantable cardiac stimulation device of FIGS. 1 and 2.

FIG. 3 illustrates pertinent components of an exemplary programmer 202 for use in programming an implantable cardiac stimulation device, including setting up electrode configurations of an implantable cardiac stimulation device. Briefly, the programmer 202 permits a physician or other authorized user to program the operation of the implantable cardiac stimulation device 110 and to retrieve and display information received from the implantable cardiac stimulation device 110 such as, EGM data and device diagnostic data. Additionally, the programmer 202 may receive and display ECG data from separate external ECG leads that may be attached to the patient. Depending upon the specific programming of the programmer, programmer 202 may also be capable of processing and analyzing data received from the implantable cardiac stimulation device 110 and from ECG leads 332 to, for example, render preliminary diagnosis as to medical conditions of the patient or to the operations of the implantable cardiac stimulation device 110.

Now, considering the components of the programmer 202 by reference to FIG. 3, operations of the programmer 202 are controlled by a CPU 302, which may be a generally programmable microprocessor or microcontroller or may be a dedicated processing device such as an application specific integrated circuit (ASIC) or the like. Software instructions to be performed by the CPU can be accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable cardiac stimulation device 110 to be programmed or may display a menu of types of diagnostic data to be retrieved and displayed. In response thereto, the physician enters various commands via either a touch screen 316 overlaid on LCD display 314 or through a standard keyboard 318 supplemented by additional custom keys 320, such as an emergency VVI (EVVI) key. The EVVI key sets the implantable cardiac stimulation device 110 to a safe VVI mode with high pacing outputs. This ensures life sustaining pacing operation in nearly all situations but by no means is it desirable to leave cardiac stimulation device 110 in the EVVI mode at all times.

Typically, the physician initially controls the programmer 202 to retrieve data stored within the implanted medical device and to also retrieve ECG data from ECG leads (examples discussed above with reference to FIGS. 1 and 2) coupled to the patient's myocardium. To this end, CPU 302 transmits appropriate signals to a telemetry circuit 322, which provides components for directly interfacing with implantable cardiac stimulation device 110. The telemetry subsystem 322 can includes its own separate CPU 324 for coordinating the operations of the telemetry subsystem 322. The main CPU 302 of the programmer 202 communicates with telemetry subsystem CPU 324 via internal bus 304. The telemetry subsystem 322 additionally includes a telemetry circuit 326 connected to a telemetry wand 328, which cooperate to receive and transmit signals electromagnetically from telemetry circuit 201 of the implantable cardiac stimulation device 110. The telemetry wand 328 is placed over the chest of the patient near the implanted cardiac stimulation device 110 to permit reliable transmission of data, over telemetric link 205, between the telemetry wand and the implantable cardiac stimulation device 110. Typically, at the beginning of the programming session, the external programming device controls the implantable cardiac stimulation device 110 via appropriate signals generated by telemetry wand 328 to output all previously recorded patient and device diagnostic information. Patient diagnostic information includes, for example, measured physiological variables data, recorded EGM data and statistical patient data such as the percentage of paced versus sensed heartbeats. Device diagnostic data includes, for example, information representative of the operation of the implantable cardiac stimulation device 110 such as lead impedances, battery voltages, battery recommended replacement time (RRT) information and the like. Data retrieved from the implantable cardiac stimulation device 110 is stored by the external programmer 202 either within a random access memory (RAM) 330, a hard drive 308, within a floppy diskette placed within a floppy drive 310, etc. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable cardiac stimulation device 110 is transferred to the programmer 202, the implantable cardiac stimulation device 110 may be further controlled perform an electrode setup algorithm of the present invention, which are described in more detail below.

The programmer 202 can also include a network interface card ("NIC") 360 to permit transmission of data to and from other computer systems via a router 362 and wide area network ("WAN") 364. Alternatively, the programmer 202 might include a modem (not shown) for communication via the public switched telephone network (PSTN). Depending upon the implementation, the modem may be connected directly to internal bus 304 may be connected to the internal bus via either a parallel port 340 or a serial port 342. Data transmitted from other computer systems may include, for example, data regarding medication prescribed, administered or sold to the patient.

The CPU 302 can include an electrode setup system 350 that can instruct the cardiac stimulation device 110 to configure switches of the switch bank 274 so that specific electrode(s) are connected as a cathode and specific electrodes are connected as an anode, in accordance with embodiments of the present invention.

The programmer 202 receives data from the implantable cardiac stimulation device 110, including parameters representative of the current programming state of the implantable cardiac stimulation device 110. Under the control of the physician, programmer 202 displays the current programming parameters and permits the physician to reprogram the parameters. To this end, the physician enters appropriate commands via any of the aforementioned input devices and, under control of the CPU 302, the programming commands are converted to specific programming parameters for transmission to the implantable cardiac stimulation device 110 via the telemetry wand 328 to thereby reprogram the implantable cardiac stimulation device 110. Prior to reprogramming specific parameters, the physician may control the external programmer to display any or all of the data retrieved from the implantable cardiac stimulation device 110, including displays of ECGs, and statistical patient information. The external programmer can also display to the physician which electrode(s) are being used as a cathode and which electrode(s) are being used as an anode when pacing and/or sensing. Any or all of the information displayed by programmer 202 may also be printed using a printer 336.

A speaker 344 is included for providing audible tones to the user, such as a warning beep in the event improper input is provided by the physician. Telemetry subsystem 322 may additionally include an input/output circuit 346 which can control the transmission of analog output signals, such as ECG signals output to an ECG machine or chart recorder. Other peripheral devices may be connected to the external programmer 202 via parallel port 340 or a serial port 342 as well. Although one of each is shown, a plurality of input output (IO) ports might be provided.

With the programmer 202 configured as shown, a physician or other authorized user can retrieve, process and display a wide range of information received from the implantable cardiac stimulation device 110 and reprogram the implantable cardiac stimulation device 110 if needed. The descriptions provided herein with respect to FIG. 3 are intended merely to provide an overview of the operation of the exemplary programmer 202 and are not intended to describe in detail every feature of the hardware and software of the device and are not intended to provide an exhaustive list of the functions performed by the device.

Exemplary Multi-Electrode Leads

Figure 4A:
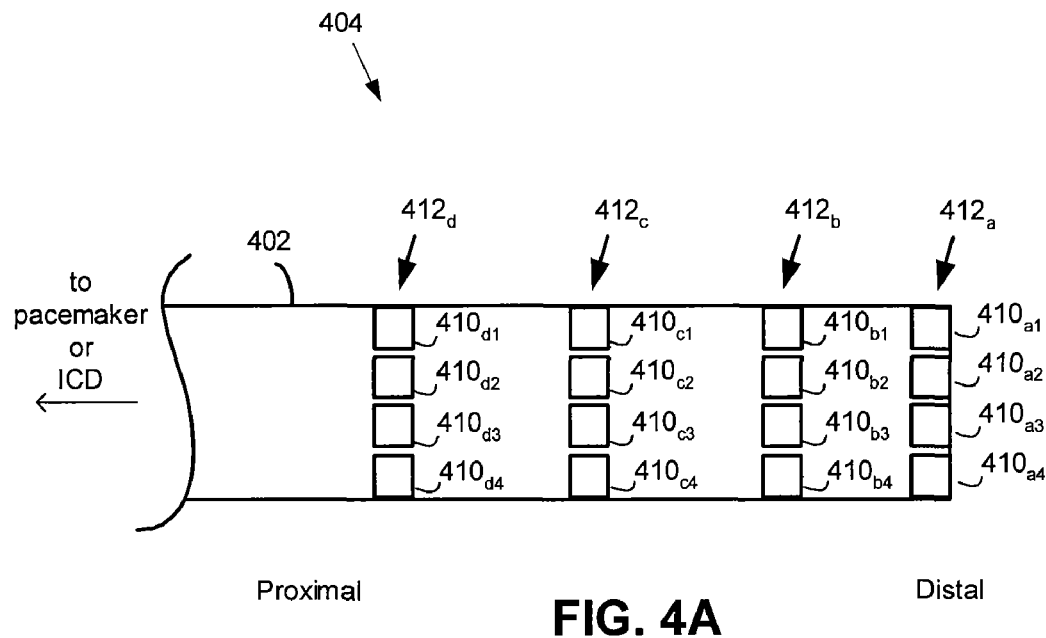
FIGS. 4A-4C schematically illustrate portions of exemplary multi-electrode leads with which embodiments of the present invention can be implemented.

FIG. 4A illustrates a portion 404 of an exemplary multi-electrode lead 402, which can be used with specific embodiments of the present invention. While not specifically shown in FIG. 4A, the lead 402 can be connected to the implantable cardiac stimulation device 110, in place of any of leads 120, 124 and/or 130. For the purpose of the following description, the lead 402 will be described as having a 4×4 matrix of electrodes, because the lead includes four arrays (also referred to as groups) of electrodes, each of which includes four electrodes 410. Each electrode 410 is electrically isolated from the other electrodes 410, but is capable of being electrically connected to other electrodes. Thus, lead 402 includes sixteen electrically isolated electrodes 410.

Figure 4B:
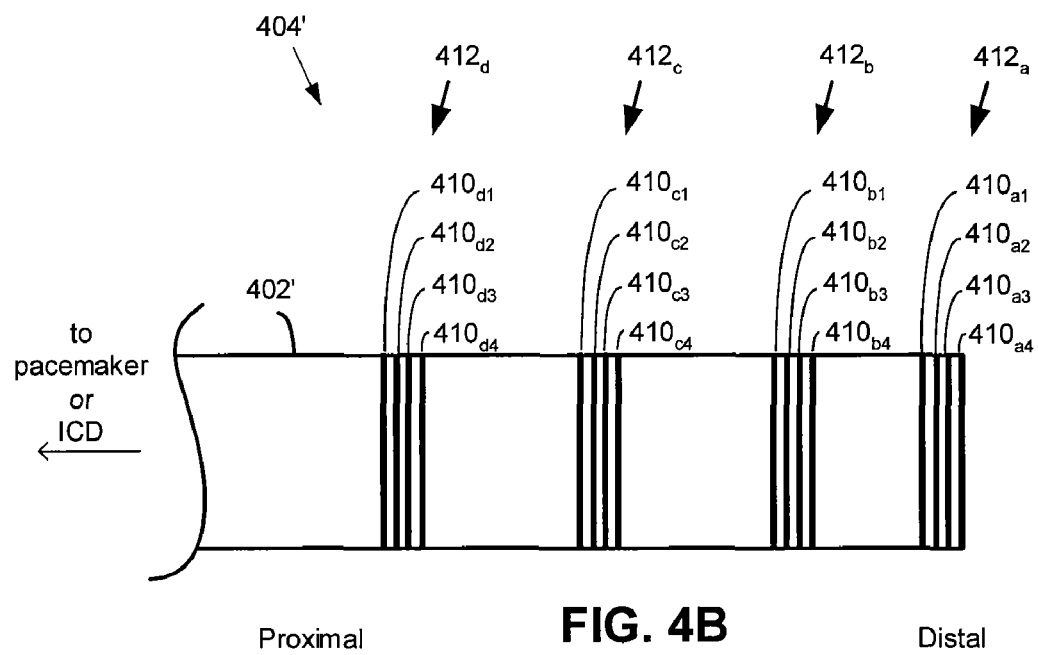
Figure 4C:
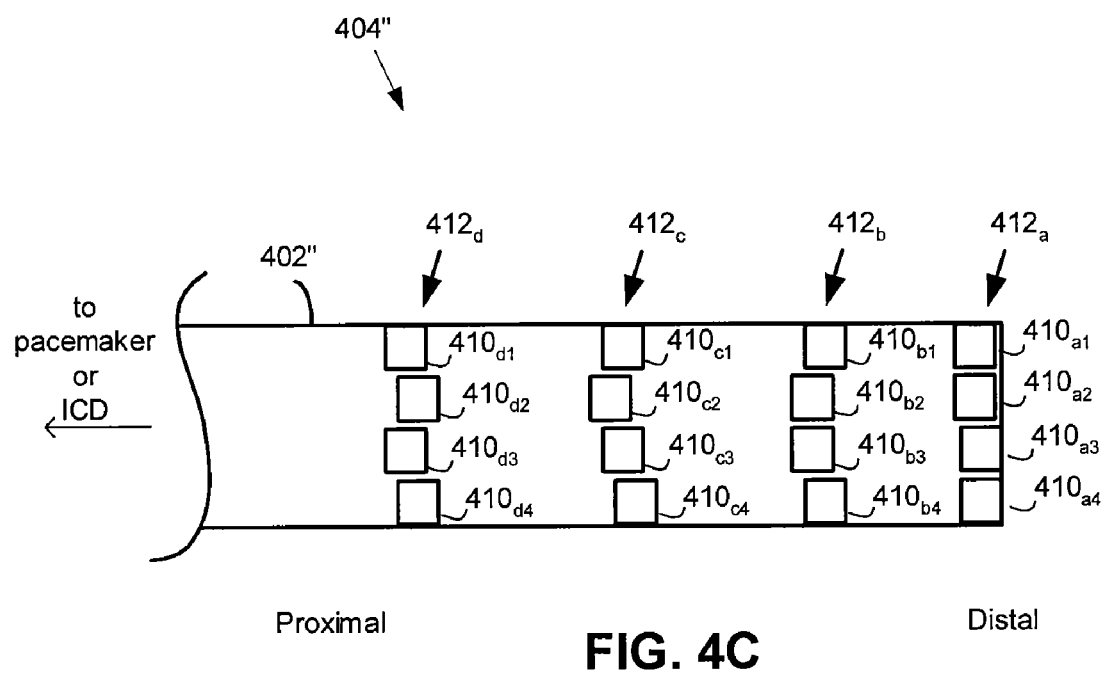

Each group of electrodes is generally located a similar distance distal from the implantable cardiac stimulation device 110 to which the lead 402 is connected. This is because electrodes of a same group are all within 5 mm of one another. As shown in FIG. 4A, a first group of electrodes $412_a$, which is most distal from the implantable cardiac stimulation device 110, includes electrodes $410_{a1}$, $410_{a2}$, $410_{a3}$ and $410_{a4}$. A second group of electrodes $412_b$, which is more proximal to the implantable cardiac stimulation device 110, includes electrodes $410_{b1}$, $410_{b2}$, $410_{b3}$ and $410_{b4}$. Also shown are a third group of electrodes $412_c$ and a fourth group of electrodes $412_d$. The groups of electrodes are shown schematically, and are not drawn to scale. For example, it may be that each electrode 410, of a group of electrodes 412, actually occupies slightly less than 90 degrees of a ring around a lead. Alternatively, electrodes 412 of a group 410 can be very closely spaced ring electrodes, e.g., as shown in FIG. 4B. FIG. 4C shows yet another example of groups 412 of electrodes 410. Other groups of electrodes are also possible, as one of ordinary skill in the art would appreciate from this description.

Electrodes of a same group are relatively close to one another, i.e., within 5 mm of one another. Electrodes of different groups are relatively further apart from one another, i.e., at least 10 mm apart.

Each electrode of a multi-electrode lead can have its own dedicated conductor through which signals can be transferred between the electrode and the implantable cardiac stimulation device (e.g., 110). For example, a multi-electrode lead disclosed in U.S. Pat. No. 6,978,178 (Sommer et al.), which is incorporated herein by reference, is shown as having seven electrodes and seven conductors. However, because of physical limitations, it is unlikely that a lead will have more than four conductors, but it is possible.

Alternatively, a multi-electrode lead can have circuitry within the lead that enable multiple electrodes to be selectively connected to a common conductor, thereby reducing the number of conductors within the lead to a more practical number. An example of such a multi-electrode lead is disclosed, for example, in U.S. Publication No. 2006/0058588 (U.S. patent application Ser. No. 11/219,305), now U.S. Pat. No. 7,214,189, issued on May 8, 2007, entitled "Methods and Apparatus for Tissue Activation and Monitoring" (Zdeblick), published Mar. 16, 2006 (filed Sep. 1, 2005), which is incorporated herein by reference above. The multi-electrode lead of the '588 patent publication includes what are referred to as "satellites", where each satellite essentially includes a group of electrodes with switching and control circuitry that enables any electrode of a group to be connected to one of two conductors. Stated another way, each group of electrodes can be said to include switching and control circuitry. Such switching and control circuitry is controlled by a controller associated with a pacemaker, to which the lead is attached. Digital signals can be sent via the two conductors from the controller to the switching and control circuitry, to thereby control which electrodes(s) is/are to be connected to which of the two conductors. Additionally, analog signals can be sent via the two conductors between the pacemaker and electrodes, for delivering pacing pulses, and sensing. The '588 patent publication discloses that one such lead can includes, e.g., eight satellites, with each satellite including four electrodes, which would result in a lead having thirty-two electrodes. The electrodes of the leads 402, 402' and 402" of FIGS. 4A, 4B, and 4C can be configured and controlled in a similar manner as those disclosed in the '588 patent publication. In other words, each group of electrodes of leads 402, 402' and 402" can include switching circuitry and control circuitry.

These are just a few examples of multi-electrode leads with which embodiments of the present invention can be used. Alternative multi-electrode leads are discussed below. However, embodiments of the present invention, unless stated otherwise, are not limited to use with the exemplary leads described herein.

Configuring a Multi-Electrode Lead

As mentioned above, pacing of the left side of the heart (i.e., left ventricle and/or left atrium) has been used, e.g., to improve cardiac function in heart failure patients. For a more specific example, left side pacing has been used for cardiac resynchronization therapy (CRT), which has been used to treat patients with congestive heart failure (CHF).

As also mentioned above, a challenge with such left side pacing is that undesirable extracardiac stimulation often occurs, especially of the diaphragm and/or the phrenic nerve. Accordingly, it would be advantageous to reduce the probability of undesirable extracardiac stimulation caused when attempting to pace the left side of the heart.

Acute canine test results using a multi-electrode lead (similar to the one described with reference to FIG. 4A) have demonstrated the ability to eliminate extracardiac stimulation in an LV (cardiac vein) implant when the electrode used as the anode and the electrode used as the cathode are within 5 mm of one another (i.e., within a same group). This can be appreciated from a comparison between FIGS. 5A and 5B.

Figures 5A, 5B:
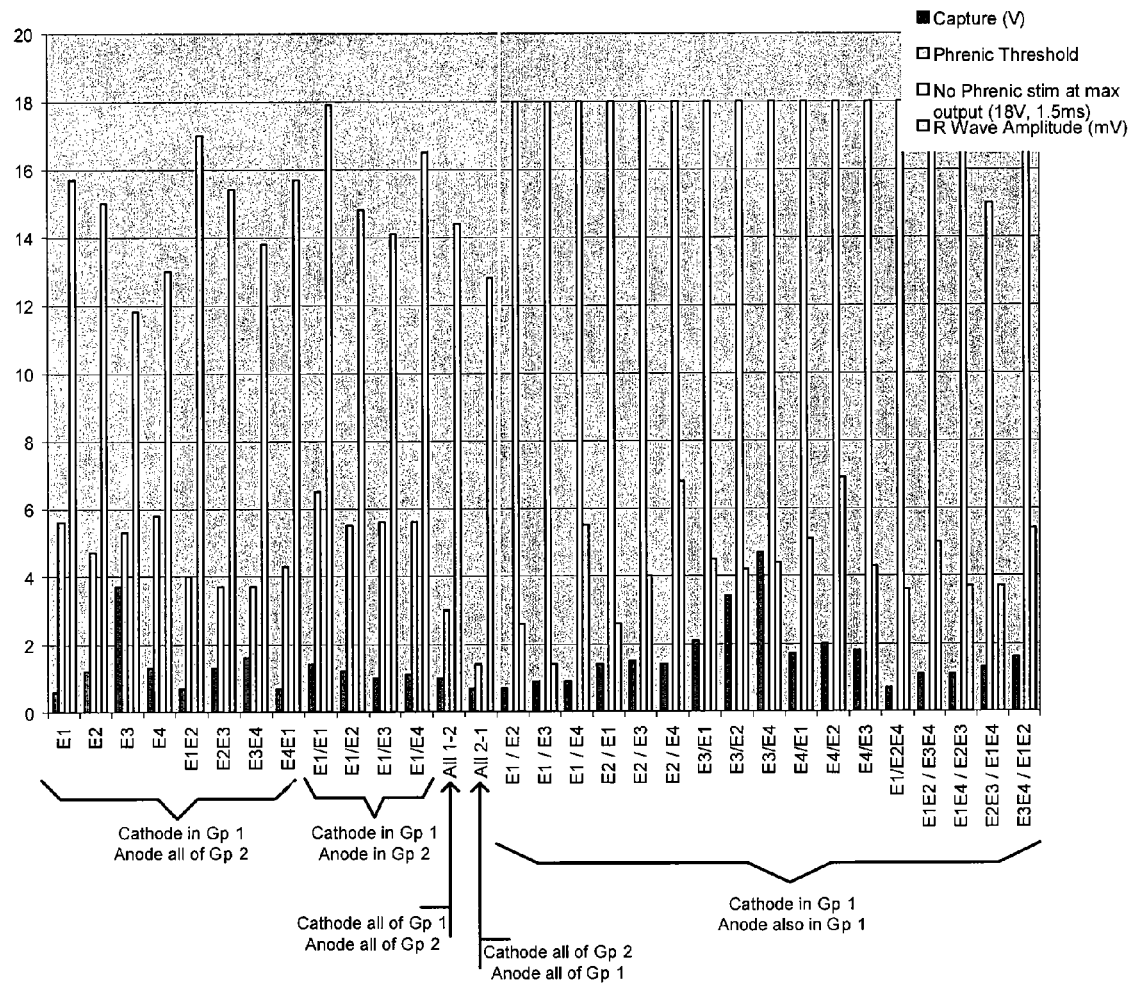
FIG. 5A is a graph that illustrates capture threshold levels, phrenic nerve stimulation levels and sensed R wave amplitudes using various configures of a multi-electrode lead (similar to the one of FIG. 4A), where the electrode(s) used as the cathode is/are at least 10 mm away from the electrode(s) uses as the anode.
FIG. 5B is a graph that illustrates capture threshold levels, phrenic nerve stimulation levels and sensed R wave amplitudes using various configurations of a multi-electrode lead (similar to the one of FIG. 4A), where the electrode(s) used as the cathode and the electrode(s) used as the anode is/are within 5 mm of each other.

FIG. 5A illustrates capture threshold levels, phrenic nerve stimulation threshold levels and sensed R wave amplitudes using various configurations of a multi-electrode lead (similar to the one described in FIG. 4A), where the cathode is one or more electrode of a first group (e.g., 412a), and the anode is one or more electrode of a second group (e.g., 412b). For example, in FIG. 5A, the three bars above the label "E1" correspond to when the cathode is electrode 1 of the $1^{st}$ group (e.g., electrode $410_{a1}$ of group $412_a$), and the anode is all the electrodes of the $2^{nd}$ group (e.g., electrodes $410_{b1}$, $410_{b2}$, $410_{b3}$ and $410_{b4}$ of group $412_b$) electrically connected together; the three bars above the label "E1E2" correspond to when the cathode is the $1^{st}$ and $2^{nd}$ electrodes of the $1^{st}$ group (e.g., electrodes $410_{a1}$ and $410_{a2}$ of group $412_a$) electrically connected together, and the anode is all the electrodes of the $2^{nd}$ group (e.g., electrodes $410_{b1}$, $410_{b2}$, $410_{b3}$ and $410_{b4}$ of group $412_b$) electrically connected together; and the three bars above the label "E1/E2" correspond to when the cathode is the $1^{st}$ electrode of the $1^{st}$ group (e.g., electrode $410_{a1}$ of group $412_a$), and the anode is the $2^{nd}$ electrode the $2^{nd}$ group (e.g., electrodes $410_{b2}$ of group $412_b$).

In FIG. 5A, capture thresholds ranged from about 0.5V to about 3.5V, which are acceptable. Sensed R wave amplitudes ranged from about 10.5V to 18V, which are also acceptable. However, to avoid phrenic nerve stimulation, the phrenic nerve stimulation threshold for an electrode configuration should be greater than the capture threshold for that electrode configuration. In summary, FIG. 5A illustrates that acceptable capture threshold levels and sensed R-wave amplitudes can be achieved by having the anode and the cathode be electrodes of separate groups (i.e., electrodes separated from one another by at least 10 mm), but that such electrode configurations result in phrenic nerve stimulation threshold levels that are lower than desired.

FIG. 5B illustrates capture threshold levels, phrenic nerve stimulation threshold levels and sensed R wave amplitudes using various configurations of a multi-electrode lead (similar to the one described in FIG. 4A), where the cathode is one or more electrode in a first group (e.g., 412a), and the anode is one or more electrodes of the same group (e.g., 412a). In other words, the electrode(s) used as the cathode is within 5 mm of the electrode(s) used as the anode. For example, in FIG. 5B, the three bars above the label "E1/E2" correspond to when the cathode is electrode 1 of the $1^{st}$ group (e.g., electrode $410_{a1}$ of group $412_a$), and the anode is electrode 2 of the $1^{st}$ group (e.g., electrode $410_{a2}$ of group $412_a$); and the three bars above the label "E1E2/E3E4" correspond to when the cathode is the $1^{st}$ and $2^{nd}$ electrodes of the $1^{st}$ group (e.g., electrodes $410_{a1}$ and $410_{a2}$ of group $412_a$) electrically connected together, and the anode is the $3^{rd}$ and $4^{th}$ electrodes of the 1st group (e.g., electrodes $410_{a3}$ and $410_{a4}$ of group $412_a$) electrically connected together.

In FIG. 5B, capture voltages ranged from about 0.5V to about 4.5V, which are acceptable. Impressively, no phrenic nerve stimulation occurred even where pacing pulses of 18V, 1.5 ms were delivered. However, sensed R wave amplitudes ranged from only about 1.5V to 4V, which is lower than desired. In summary, FIG. 5B illustrates that acceptable capture threshold levels, and avoidance of phrenic nerve stimulation can be achieved by having the anode and the cathode be electrodes of the same group (i.e., within 5 mm of one another), but that such electrode configurations result in sensed R-wave amplitudes lower than desired.

It is believed that embodiments of the present invention overcome the deficiencies of the electrode configurations discussed above with reference to FIGS. 5A and 5B by using what shall be referred to as a "distributed" anode. More specifically, it is believed that embodiments of the present invention will provide for good sensed R wave amplitudes by having an electrode used as an anode be at least 10 mm from the electrode(s) used the cathode, but also avoid extracardiac stimulation by having an electrode also used as the anode be within 5 mm of the electrode(s) used as the cathode. It is believe that embodiments of the present invention will provide capture threshold levels and sensed R wave amplitudes similar to those shown in FIG. 5A, while also avoiding phrenic and other extracardiac nerve stimulation as was shown with reference to FIG. 5B.

Figure 6A:
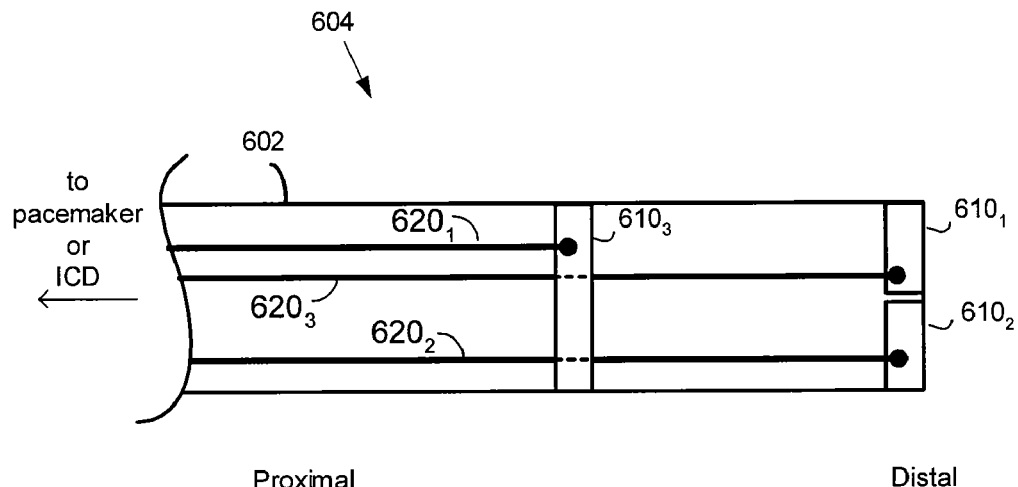
FIG. 6A illustrates a portion of an exemplary three electrode/three conductor lead, which can be used to implement embodiments of the present invention.
Figure 6B:
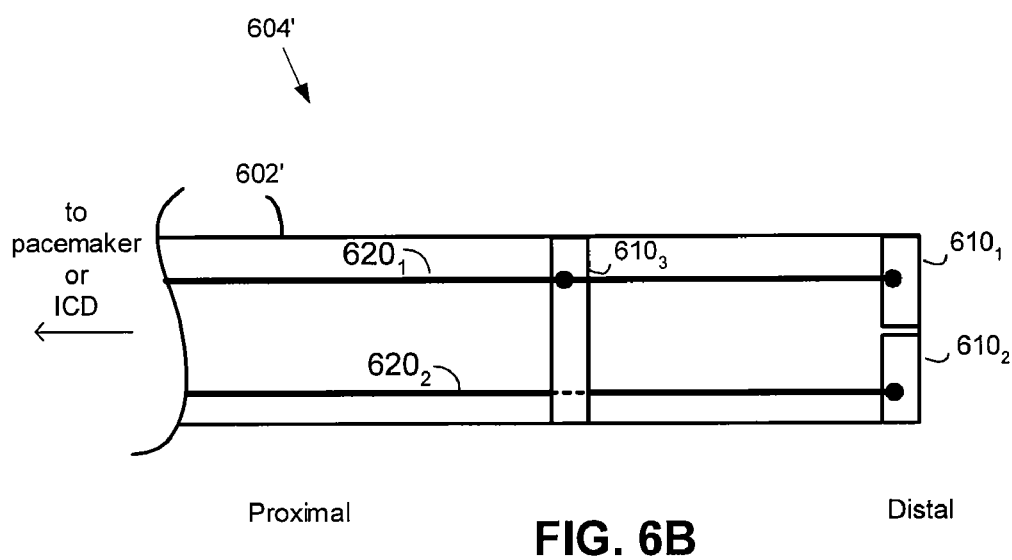
FIG. 6B illustrates a portion of a three electrode/two conductor lead, according to an embodiment of the present invention.

FIGS. 4A, 4B and 4C discussed above illustrate exemplary leads 402, 402' and 402" that each have four groups of electrodes, with each group of electrodes including four groups, resulting in each lead having a total of 16 electrodes. Such leads can be used to implement embodiments of the present invention. When using a lead such as those in FIGS. 4A, 4B and 4C, the cathode can be one or more electrode in a group, and the anode can be one or more electrode of that same group electrically connected with one or more electrode of another group. However, embodiments of the present invention are not limited to use with multi-electrode leads that are similar to those described with reference to FIGS. 4A, 4B and 4C. Rather, certain embodiments of the present invention can be used with any lead that includes two electrodes that are within 5 mm of each other, and another electrode at least 10 mm from the two electrodes within 5 mm of each other. Examples of such leads are shown in FIGS. 6A and 6B. Other embodiments of the present invention only require a lead having a least two electrodes within 5 mm of on another. Unless stated otherwise, separate electrodes are presumed to be electrically isolated from one another, as are separate conductors (i.e., conductive paths).

Referring to FIG. 6A, a portion 604 of lead 602 is shown as including three electrically isolated conductors and three electrodes. More specifically, the lead 602 includes two electrodes $610_1$ and $610_2$ that are within 5 mm of one another, which are shown as being located at the distal end of the lead 602, but that is not necessary. The lead is also shown as including a further electrode $610_3$, which is at least 10 mm from the two electrodes $610_1$ and $610_2$. Electrodes $610_1$ and $610_2$ can be, e.g., tip electrodes, but are not limited thereto. Electrode $610_3$ can be a ring or coil electrode, but is not limited thereto. Each electrode is shown as having its own hardwired conductor $620_1$, $620_2$ and $620_3$. Alternatively, since electrodes $610_1$ and $610_3$ are both being used as the anode when pacing and sensing, they can both be hardwired to the same conductor $620_1$, as shown in FIG. 6B. The lead of 602' of FIG. 6B is especially useful with implantable stimulation devices that are not capable of connecting to and/or functioning with leads having more than two conductors.

In FIGS. 6A and 6B, the electrode configured as the cathode has been shown as being an electrode located at or near the distal end of a lead, where at least one electrode configured as the anode is proximal the distal end. However, this need not be the case. In other words, it is within the scope of the present invention that one of the electrodes configured as part of the distributed anode be more distal than the electrode(s) configured as the cathode. It is also noted that while the "first" group is shown as being more distal than the "second" group in the FIGS., the terms "first" and "second" are not intended to represent a specific order or location, but rather are used for distinguishing between multiple elements of the same type.

Figure 7:
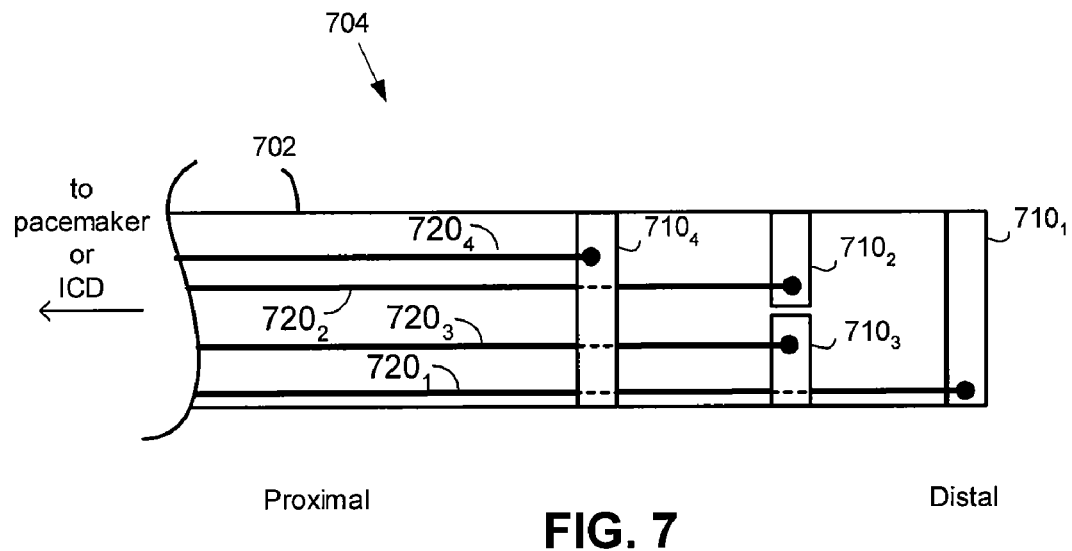
FIG. 7 illustrates a four electrode/four conductor lead, that can be used to implement specific embodiments of the present invention.

FIG. 7 illustrates a portion 704 of a lead 702 including four electrically isolated conductors and four electrodes. More specifically, the lead 702 includes four electrodes $710_1$, $710_2$, $710_3$ and $710_4$. Electrodes $710_2$ and $710_3$ are each half of a ring, and are considered electrodes of the same group (Group 1) since they are within 5 mm of one another. The ring electrode $710_4$ is part of a separate group (Group 2), since it is at least 10 mm from the electrodes $710_2$ and $710_3$ of Group 1. The tip electrode $710_1$ is part of a further group (Group 3). Each electrode is connected to a corresponding one of the conductors 720.

Figure 8:
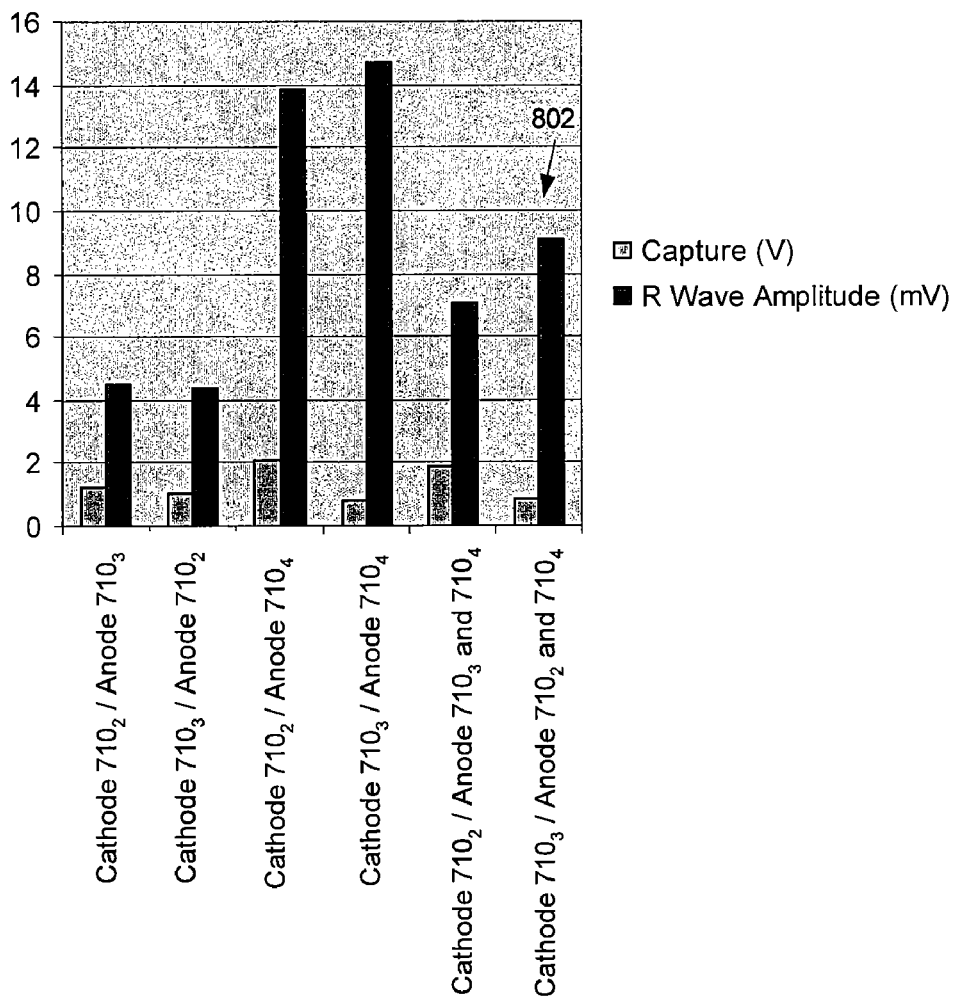
FIG. 8 is a graph that illustrates capture threshold levels and sensed R wave amplitudes achieved using various configurations of the lead of FIG. 7.

FIG. 8 shows capture threshold levels and sensed R wave amplitudes achieved for various cathode and anode combinations using the lead 702 of FIG. 7 (note that the tip electrode $710_1$ was not used in any of the tested combinations). From the last data set 802 in FIG. 8 (where the electrode $710_3$ was used as the cathode and the electrodes $710_2$ and $710_4$ were both used as the anode) it can be appreciated that a desired low capture threshold level and desired high R wave amplitude can be achieved using a distributed anode configuration. From the results shown in FIGS. 5A and 5B, it can also be hypothesized that such a distributed anode configuration will also provide for a high phrenic nerve threshold, which is also desired. In other words, a distributed anode configuration can be used to achieve a sufficiently low capture threshold level, and to sense R waves of sufficient amplitude, while also avoiding phrenic nerve and other extracardiac stimulation.

In accordance with specific embodiments of the present invention, at least a first electrode and a second electrode of a lead are within 5 mm of one another, with the first electrode configured as the cathode, the second electrode configured as the anode, and at least a third electrode (at least 10 mm from the first and second electrodes) of the same lead also configured as the anode. Such a "third" electrode, however, need not be on the same lead as the "first" and "second" electrodes. Rather, in specific embodiments, the conductive housing (e.g., 240) of the implantable cardiac device (to which the lead having the "first" and "second" electrodes is attached) can be configured as the "third" electrode. In other words, a conductive device housing (e.g., 240) can function as part of the distributed anode. In other embodiments, the "third" electrode configured as part of the distributed anode can be on a separate lead than the "first" and "second" electrodes. The term "distributed" anode is used herein because at least two electrodes, that are distributed at least 10 mm apart from one another, are used together as the anode.

Many of the above embodiments of the present invention are now summarized. Such embodiments can be used for pacing and sensing in a chamber of a patient's heart using a lead that includes a first group of at least two electrically isolated electrodes within 5 mm of one another. Such embodiments include when both pacing and sensing, using as a cathode at least one of the electrodes of the first group; and when both pacing and sensing, using as an anode at least one of the electrodes of the first group that is not used as the cathode, together with a further electrode that is at least 10 mm from the first group. As mentioned above, the "further electrode", which is used as part of the distributed anode, can be an electrode of the same lead as the electrodes of the first group, or an electrically conductive device housing to which the lead is connected. It is also within the scope of the present invention that the "further electrode" that is used as part of the distributed anode be an electrode of a separate lead. A lead used to implement embodiments of the present invention can be similar to those described with reference to FIGS. 4A, 4B and 4C, or similar to those described with reference to FIGS. 6A and 6B, but are not limited thereto.

While especially useful for pacing and sensing in the left ventricle of a patient's heart, embodiments of the present invention can be used for pacing and sensing in other cardiac chambers.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use when pacing and sensing in a chamber of a patient's heart using a lead that includes a first group of at least two electrically isolated electrodes within 5 mm of one another and using a further electrode that is at least 10 mm from the first group, comprising:
    (a) when pacing, using as a pacing cathode at least one of the electrodes of the first group;
    (b) when pacing, using as a pacing anode at least one of the electrodes of the first group that is not used as the pacing cathode, together with the further electrode that is at least 10 mm from the first group also being used as the pacing anode;
    (c) when sensing, using as the sensing cathode the same electrode(s) that is/are used as the pacing cathode when pacing at step (a); and
    (d) when sensing, using as the sensing anode the same electrodes that are used as the pacing anode when pacing at step (b).

2. The method of claim 1, wherein the lead includes the further electrode.

3. The method of claim 2, wherein the further electrode comprises a ring electrode.

4. The method of claim 2, wherein the further electrode comprises a coil electrode.

5. The method of claim 2, wherein:
    the lead includes first and second electrically isolated conductors;
    one of the first group of electrodes is hardwired to the first conductor;
    another one of the first group of electrodes is hardwired to the second conductor; and
    the further electrode, which is at least 10 mm from the first group of electrodes, is also hardwired to the second conductor.

6. The method of claim 1, wherein the further electrode is an electrode of a further lead.

7. The method of claim 1, wherein the lead is connected to an implantable cardiac stimulation device having a conductive housing; and
    step (b) includes using as the pacing anode at least one of the electrodes of the first group that is not used as the pacing cathode, together with the conductive housing also being used as the pacing anode.

8. The method of claim 1, wherein the lead is configured such that the first group of electrodes can be placed in a patient's left ventricle.

9. The method of claim 1, wherein the lead includes a second group of at least two electrically isolated electrodes within 5 mm of one another, which are at least 10 mm from the first group; and
    step (b) includes using as the pacing anode at least one of the electrodes of the first group that is not used as the pacing cathode, together with at least one of the electrodes of the second group also being used as the pacing anode.

10. The method of claim 9, wherein:
    the lead includes first and second electrically isolated conductors;
    each group of electrodes includes switching circuitry to selectively connect each electrode of the group to either of the conductors; and
    step (a) includes connecting as the pacing cathode one of the electrodes of the first group; and
    step (b) includes connecting as the pacing anode one of the electrodes of the first group that is not used as the pacing cathode, together with one of the electrodes of the second group also being connected as the pacing anode.

11. The method of claim 10, wherein:
    step (a) includes configuring the switching circuitry of the first group to connect at least one of the electrodes of the first group to the first conductor; and step (b) includes
- configuring the switching circuitry of the first group to connect at least one of the other electrodes of the first group to the second conductor; and
- configuring the switching circuitry of the second group to connect at least one of the electrodes of the second group to the second conductor.

12. An implantable cardiac stimulation system, comprising:
pacing circuitry;
sensing circuitry;
a lead that includes a first group of at least two electrically isolated electrodes within 5 mm of one another; and
a further electrode that is at least 10 mm from the first group;
wherein, during pacing,
- a pacing cathode operably connected to the pacing circuitry includes at least one of the electrodes of the first group, and
- a pacing anode operably connected to the pacing circuitry includes at least one of the electrodes of the first group that is not used as the pacing cathode, together with the further electrode that is at least 10 mm from the first group also operably connected to the pacing circuitry as the pacing anode; and wherein, during sensing,
- a sensing anode includes the same electrodes as the pacing anode that are instead operably connected to the sensing circuitry, and
- a sensing cathode includes the same electrode(s) as the pacing cathode that is/are instead operably connected to the sensing circuitry.

13. The system of claim 12, wherein the lead includes the further electrode.

14. The system of claim 13, wherein the further electrode comprises a ring electrode.

15. The system of claim 13, wherein the further electrode comprises a coil electrode.

16. The system of claim 13, wherein:
the lead includes first and second electrically isolated conductors;
one of the first group of electrodes is hardwired to the first conductor;
another one of the first group of electrodes is hardwired to the second conductor; and
the further electrode, which is at least 10 mm from the first group of electrodes, is also hardwired to the second conductor.

17. The system of claim 12, further comprising:
a further lead;
wherein the further electrode is an electrode of the further lead.

18. The system of claim 12, further comprising:
a plurality of switches;
wherein the switches are configured to enable the pacing circuitry to pace in a chamber of the patient's heart, and the sensing circuitry to sense in the chamber of the patient's heart.

19. The system of claim 18, further comprising:
a conductive housing within which are located the pacing circuitry, the sensing circuitry, and the switches; and
the switches are configured to enable the pacing circuitry to pace in a chamber of the patient's heart, and the sensing circuitry to sense in the chamber of the patient's heart, using as the anode at least one of the electrodes of the first group together with the conductive housing.

20. The system of claim 12, wherein the lead is configured such that the first group of electrodes can be placed in a patient's left ventricle.

21. The system of claim 18 wherein the lead includes a second group of at least two electrically isolated electrodes within 5 mm of one another, which are at least 10 mm from the first group; and
the switches are configured to enable the pacing circuitry to pace in a chamber of the patient's heart, and the sensing circuitry to sense in the chamber of the patient's heart, using as the anode at least one of the electrodes of the first group that is not used as the cathode, together with at least one of the electrodes of the second group also being used as the anode.

22. The system of claim 21, wherein:
the lead includes first and second electrically isolated conductors;
each group of electrodes includes switching circuitry to selectively connect each electrode of the group to either of the conductors; and
wherein the switching circuitry of the first group is configured to connect at least one of the electrodes of the first group to the first conductor and at least one other electrode of the first group to the second conductor; and
wherein the switching circuitry of the second group is configured to connect at least one of the electrodes of the second group to the second conductor.

23. The system of claim 12, wherein, during sensing, the sensing cathode includes the at least one of the electrodes of the first group, and the sensing anode includes the at least one of the electrodes of the first group that is not used as the sensing cathode, together with the further electrode that is at least 10 mm from the first group also being used at the sensing anode.

24. A lead, comprising:
first and second electrically isolated conductors;
first and second electrically isolated electrodes within 5 mm of one another; and
a third electrode at least 10 mm from the first and second electrodes;
wherein the first electrode is hardwired to the second conductor for use as a cathode; and
wherein the second and third electrodes are hardwired to the first conductor for use as an anode at the same time.

25. The lead of claim 24, wherein there is always an electrical short between the second and the third electrode.

* * * * *